United States Patent [19]
Baron

[11] Patent Number: 4,712,543
[45] Date of Patent: Dec. 15, 1987

[54] PROCESS FOR RECURVING THE CORNEA OF AN EYE

[76] Inventor: Neville A. Baron, Medical Plz. #66, Rte. 46, Dover, N.J. 07801

[21] Appl. No.: 633,197

[22] Filed: Jul. 23, 1984

Related U.S. Application Data

[63] Continuation-in-part of Ser. No. 340,978, Jan. 20, 1982, Pat. No. 4,461,294.

[51] Int. Cl.⁴ .......................................... A61B 17/36
[52] U.S. Cl. .................................................. 128/303.1
[58] Field of Search .................. 128/303.1, 395–398

[56] References Cited

U.S. PATENT DOCUMENTS

| | | | |
|---|---|---|---|
| 3,703,176 | 11/1972 | Vassiliadis et al. | 128/395 |
| 3,783,874 | 1/1974 | Koester et al. | 128/395 |
| 3,900,034 | 8/1975 | Katz et al. | 128/395 |

FOREIGN PATENT DOCUMENTS

| | | | |
|---|---|---|---|
| 2361672 | 7/1974 | Fed. Rep. of Germany | 128/303.1 |
| 1184814 | 3/1970 | United Kingdom | 128/395 |
| 563751 | 12/1977 | U.S.S.R. | 128/303.1 |

*Primary Examiner*—Lee S. Cohen
*Attorney, Agent, or Firm*—Eric P. Schellin

[57] ABSTRACT

A process for predictably recurving the cornea of an eye by disposing light-absorbing color bodies in the cornea, and then vaporizing at least some of the color bodies with light energy according to a predetermined pattern to form corneal-recurving scars. The light energy is focused in the cornea and defocused and diffused behind the cornea. The color bodies used are of a transient nature, and those not vaporized fade and disperse out of the cornea in due course.

5 Claims, 2 Drawing Figures

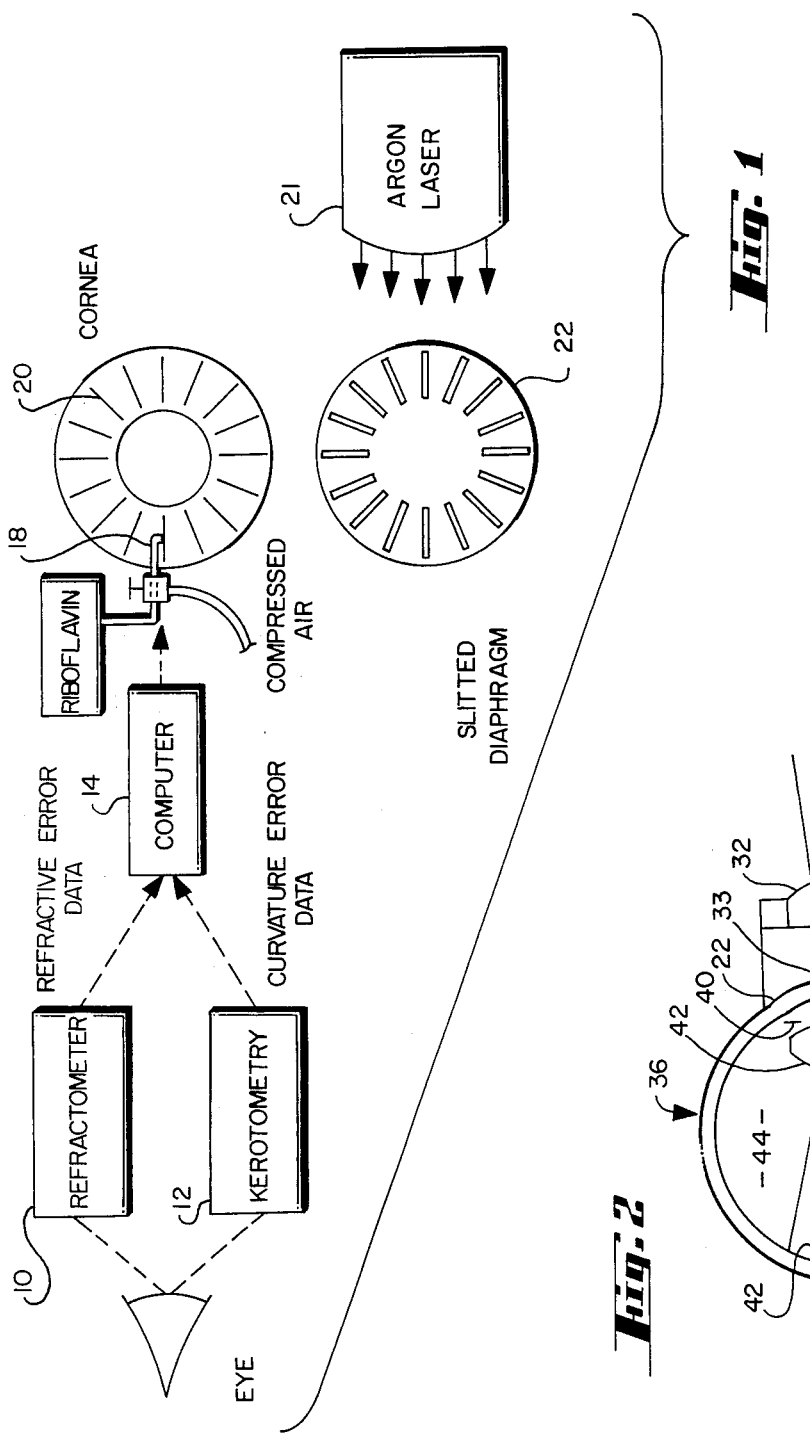

PROCESS FOR RECURVING THE CORNEA OF AN EYE

This application is a continuation-in-part of my co-pending application Ser. No. 340,978, filed Jan. 20, 1982, now U.S. Pat. No. 4,461,294 dated July 24, 1984.

BACKGROUND OF THE INVENTION

This invention relates to an apparatus and process for recurving the cornea of an eye.

It has previously been proposed to recurve the cornea of an eye by a surgical procedure (radial keratotomy) in which spoke-like incisions are made in the cornea using microsurgery techniques. However, this procedure is difficult to control precisely.

It has also previously been proposed to utilize light energy (transmitted through the iris in some instances) to effect photocoagulation in the treatment of surface, skin, and conjunctival lesions, as well as retinal tears. In this regard it has been reported that problems encountered with inadvertent overheating of the anterior segment secondary to photocoagulation include serofibrinous iritis, posterior and anterior synechias, corneal endothelial edema, swelling of the corneal stroma, epithelial corneal edema, secondary glaucoma, iris atrophy, corneal dystrophy, and progressive cataract. It has also been stated that sufficient absorption of light energy by the iris may lead to iris atrophy, irregularity of the pupil, and other symptoms, that excessive photocoagulation may cause tissue shrinkage leading to traction or displacement of tissues, and that "Without direct treatment to the cornea, corneal leukomas, which are usually transient, and corneal neovascularization rarely have been reported with an inadequately dilated pupil". (See "Clinical Ophthalmology", Vol, 5, Chap. 9, pp. 8 and 9, published 1976 by Harper and Row, Publishers, Inc., Hagerstown, Md.)

SUMMARY OF THE INVENTION

In accordance with the present invention, apparatus for receiving the cornea of an eye comprises means for disposing light-absorbing color bodies in a cornea, and a laser adapted to vaporize said color bodies from said cornea according to a predetermined design, whereby recurving scars are generated in said cornea in accordance with said predetermined design.

Also in accordance with the present invention is a process for recurving the cornea of an eye which comprises disposing light-absorbing color bodies in a cornea according to a preselected design and thereafter vaporizing at least a portion of said design by applying energy thereto sufficient to effect vaporization thereof and generate thereby formation of scar tissue to form corneal-recurving scars in said cornea according to said preselected design.

BRIEF DESCRIPTION OF THE DRAWING

FIG. 1 shows an apparatus for carrying out the process of the invention, and

FIG. 2 shows an alternate apparatus for carrying out a variation in the process in which light energy is focused at the cornea and defocused within the eye behind the cornea.

DETAILED DESCRIPTION OF THE INVENTION

In carrying out the present invention according to a preferred embodiment thereof as illustrated in FIG. 1, the refractive error of the eye to be corrected is determined using a refractometer 10 in the usual manner. The existing curvature of the cornea is ascertained as customary by the use of kerotometry 12. The refractive error and curvature data are entered into a preprogrammed computer 14 which calculates and presents an output representing the requisite number, lengths, depths and relative positions of laser-generated incisions required to correct the corneal curvature. Typically, this pattern is toroidal and will comprise sixteen radial spokes, and will have an inner diameter of about 5 mm., an outer diameter of about 12 mm., and be centered on the cornea.

The epithelium layer of the cornea is then debrided (leaving Bowmans membrane intact) using 20% cocaine in saline solution applied manually on a cotton-tipped stick applicator.

Riboflavin dye is then applied to the cornea in bands or spokes according to the previously calculated pattern using an air jet hypodermic injection nozzle 18. The dye penetrates through Bowmans layer and into the stroma to form therein a pigmented centerless starburst of colored bands or spokes 20 according to the pattern precalculated by the computer 14.

The colored bands or spokes embedded in the cornea are thereupon vaporized by exposure to light from an Argon laser 21 adjusted to deliver monochromatic light at a frequency maximally absorbed by the riboflavin, with essentially no injury to other tissues of the eye outside the cornea.

The laser light is applied through a slitted diaphragm 22 having a pattern of slits corresponding to and aligned with the pattern calculated by the computer and used previously in the application of the riboflavin dye. Thus, the dye and the dye-vaporizing light energy are applied to the cornea according to a single, previously calculated pattern, to generate in the cornea sixteen radially disposed scars corresponding to that pattern.

Alternatively to the use of a slitted diaphragm, fiber optics may be used to deliver laser light to a housing in the shape of a contact lens having a patterned screen in direct contact with the cornea.

Following generation of the desired scar pattern in the cornea as described, antibiotic ointment is applied thereto and the eye is patched until the epithelium regenerates, typically a period of 48-72 hours, thereby establishing a healthy cornea correctively recurved to reduce both myopia and astigmatism.

In an alternate procedure, riboflavin dye is applied as a toroidal design covering the entire cornea with the exception of a 4 mm. diameter central opening centered on the pupil, and laser energy is applied thereto according to the aforesaid calculated design to generate the appropriate scar tissue. Unvaporized riboflavin fades and disperses over the normal course within a period of a few days. A suitable means for carrying out such a procedure is illustrated in FIG. 2.

As shown in FIG. 2, a converging beam 30 of monochromatic coherent light from an Argon laser (such as is indicated by reference character 21 in FIG. 1) is focused by a strongly convex 16 mm.-diameter glass lens assembly of the Goldman type 32 as a very small spot 33 at the dye-carrying stroma portion of the cornea 34 of an eye indicated generally by reference character 36. The rear surface 38 of the lens assembly 32 is disposed against the outermost forward surface of the eye 36.

As the light beam passes beyond the cornea into the eye through the pupil 40, the lens 42, the vitreous humor 44, and falls upon the retine 46, it is defocused and diverges. Thus, maximum light energy per unit area is concentrated at the plane of the absorbed color bodies, and the light energy is substantially diffused as it passes further into the eye.

The rear concave surface 38 of the Goldman lens assembly 32 is covered with a thin, light-opaque metallic coating into which a pattern of light-transmitting slits is etched to form, in effect, a slitted diaphragm (as illustrated at 22 in FIG. 1) on the back of the lens assembly. These slits may be of various widths, typically in the range of from 2.5+/−1.5 microns to 20 microns.

In use, a lens assembly is selected which has a suitable rear slit pattern for the corrections to be made. The lens assembly is positioned in contact with, and centered on, the front of the eye, to which color bodies have been applied in a torodial or annular pattern as described hereinabove. The light source for the laser beam 30 is then moved to cause the focused spot 33 to traverse only those light-passing slits selected, and for only those lengths thereof selected, for application of the appropriate pattern of light energy to the pigmented or color body-carrying stroma portion of the cornea 34. Using this technique, the slit-carrying lens assembly may be re-used, and a minimum number of variously patterned slit-carrying lens assemblys are required to permit generation of a wide selection of predetermined patterns of corneal-recurving scar tissue.

As yet another embodiment, a variety of concavo-convex opaque diaphragms of uniform thickness having light-transmitting slits therein patterned as described herein may be provided for interchangeable application to the rear face of a lens assembly of the Goldman type, the rear face of the assembly and the diaphragms having the same radius of curvature, which corresponds to that typical of the front surface of an eye.

Although riboflavins are the preferred color bodies for use in carrying out the present invention, other color bodies, preferably of a transient nature when applied to the cornea, may also be employed, e.g., red corpuscles recovered from the blood of the person undergoing corneal recurvature.

Similarly, although laser energy is preferred for use as an energy source in that a wavelength may be selected which is maximally absorbed by the color body applied to the cornea, other monochromatic, filtered, or broad spectrum sources (such as an electric arc) may likewise be employed for the purpose.

What is claimed is:

1. A process for predictably recurving the cornea of an eye which comprises disposing light-absorbing color bodies in said cornea and thereafter vaporizing at least some of said color bodies by applying thereto light energy focused thereon and defocused within said eye behind said cornea, said vaporization being effected according to a preselected patterned design and generating thereby corneal recurving scar tissue in said cornea according to said preselected patterned design.

2. A process as set forth in claim 1 in which said color bodies are disposed in the stroma layer of said cornea and said light energy is focused thereon by a light-converging lens.

3. A process as set forth in claim 2 in which said light-converging lens is disposed at, and centered on, the forward surface of said cornea.

4. A process as set forth in claim 2 in which a slitted diaphragm is interposed between said lens and said cornea, said diaphragm being opaque to light energy and the slits therein being transparent to light energy.

5. A process as set forth in claim 2 in which said light energy focused on the stroma layer is moved on said layer by moving a source of light relative to said light-converging lens.

* * * * *